(12) United States Patent
Yan et al.

(10) Patent No.: US 10,304,198 B2
(45) Date of Patent: May 28, 2019

(54) AUTOMATIC MEDICAL IMAGE RETRIEVAL

(71) Applicant: Siemens Medical Solutions USA, Inc., Malvern, PA (US)

(72) Inventors: Zhennan Yan, South River, NJ (US); Yiqiang Zhan, Berwyn, PA (US); Shu Liao, Chester Springs, PA (US); Yoshihisa Shinagawa, Downingtown, PA (US); Xiang Sean Zhou, Exton, PA (US); Matthias Wolf, Coatesville, PA (US)

(73) Assignee: Siemens Healthcare GmbH, Erlangen (DE)

( * ) Notice: Subject to any disclaimer, the term of this patent is extended or adjusted under 35 U.S.C. 154(b) by 78 days.

(21) Appl. No.: 15/705,765

(22) Filed: Sep. 15, 2017

(65) Prior Publication Data

US 2018/0089840 A1     Mar. 29, 2018

Related U.S. Application Data

(60) Provisional application No. 62/399,652, filed on Sep. 26, 2016.

(51) Int. Cl.
*G06T 7/00*          (2017.01)
*G06T 7/246*       (2017.01)
(Continued)

(52) U.S. Cl.
CPC .......... *G06T 7/248* (2017.01); *G06K 9/00288* (2013.01); *G06K 9/6255* (2013.01); *G06K 9/6256* (2013.01); *G06K 9/78* (2013.01); *G06N 5/02* (2013.01); *G06T 5/50* (2013.01); *G06T 7/0014* (2013.01); *G06T 7/97* (2017.01);
*G16H 15/00* (2018.01); *G16H 30/20* (2018.01); *G16H 30/40* (2018.01); *G16H 50/20* (2018.01); *G06K 2009/2045* (2013.01);
(Continued)

(58) Field of Classification Search
CPC ....... G06T 7/0012; G06T 7/0014; G06T 7/10; G06T 7/11; G06T 2207/20021; G06T 2207/20081; G06T 2207/30061; G06T 2207/30064; G06K 9/6255; G06K 9/6256; G06K 9/6267; G06K 2209/051; G16H 15/00; G16H 30/20; G16H 30/40; G16H 50/20; G06F 19/34
See application file for complete search history.

(56) References Cited

U.S. PATENT DOCUMENTS 10,140,421 B1 * 11/2018 Bernard et al. ........ G06F 19/321
2018/0276498 A1 * 9/2018 Madabhushi et al. ....................... G06K 9/6227

* cited by examiner

*Primary Examiner* — Andrew W Johns

(57) ABSTRACT

A framework for automatic retrieval of medical images. In accordance with one aspect, the framework detects patches in a query image volume that contain at least a portion of an anatomical region of interest by using a first trained classifier. The framework determines disease probabilities by applying a second trained classifier to the detected patches, and selects, from the patches, a sub-set of informative patches with disease probabilities above a pre-determined threshold value. For a given patch from the sub-set of informative patches, the framework retrieves, from a database, patches that are most similar to the given image. Image volumes associated with the retrieved patches are then retrieved from the database. A report based on the retrieved image volumes may then be generated and presented.

20 Claims, 7 Drawing Sheets

(51) Int. Cl.
  *G06K 9/62*   (2006.01)
  *G06K 9/00*   (2006.01)
  *G06N 5/02*   (2006.01)
  *G06K 9/78*   (2006.01)
  *G06T 5/50*   (2006.01)
  *G16H 30/40*  (2018.01)
  *G16H 30/20*  (2018.01)
  *G16H 50/20*  (2018.01)
  *G16H 15/00*  (2018.01)
  *G06K 9/20*   (2006.01)
  *G06N 20/00*  (2019.01)

(52) U.S. Cl.
  CPC ....... *G06K 2209/051* (2013.01); *G06N 20/00* (2019.01); *G06T 2207/10081* (2013.01); *G06T 2207/20212* (2013.01); *G06T 2207/30004* (2013.01)

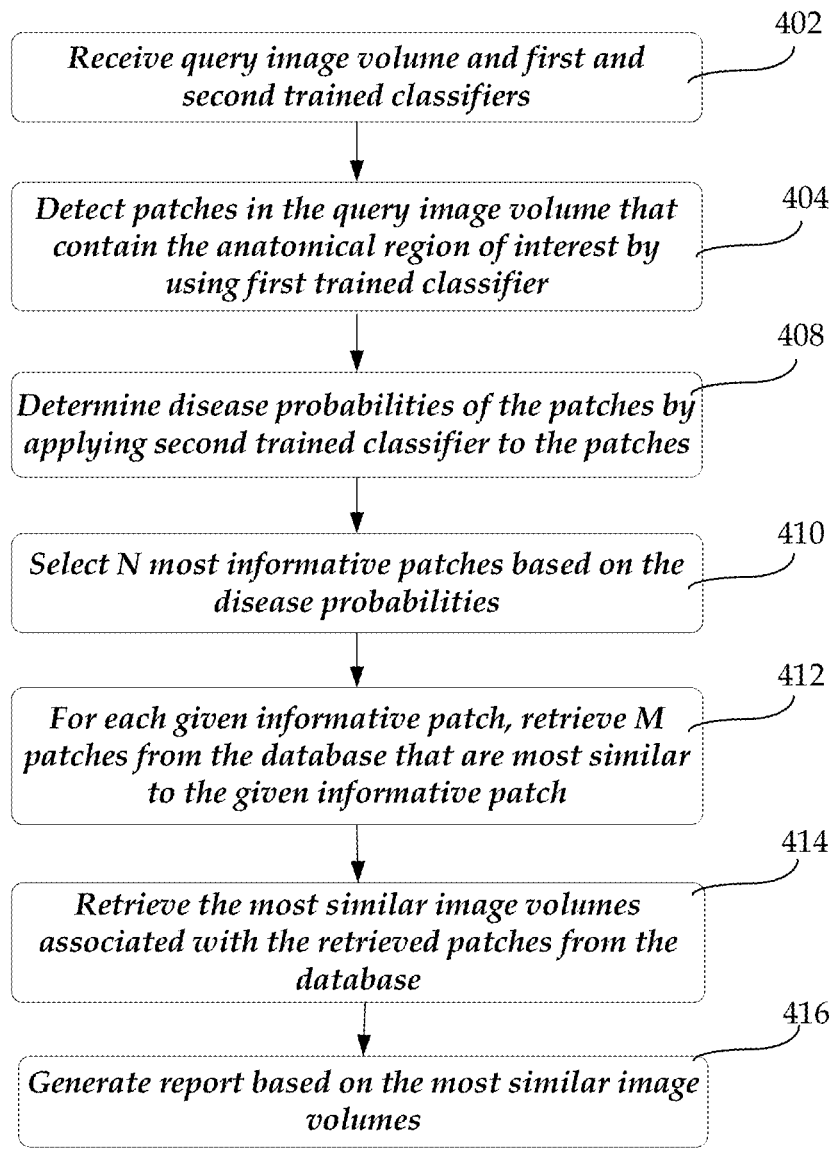

AUTOMATIC MEDICAL IMAGE RETRIEVAL

CROSS-REFERENCE TO RELATED APPLICATION

The present application claims the benefit of U.S. provisional application No. 62/399,652 filed Sep. 26, 2016, the entire contents of which are herein incorporated by reference.

TECHNICAL FIELD

The present disclosure generally relates to digital medical image data processing, and more particularly to automatic retrieval of medical images from a database.

BACKGROUND

The field of medical imaging has seen significant advances since the time X-Rays were first used to determine anatomical abnormalities. Medical imaging hardware has progressed from modern machines, such as Magnetic Resonance (MR) imaging scanners, Computed Tomographic (CT) scanners and Positron Emission Tomographic (PET) scanners, to multimodality imaging systems such as PET-CT and PET-MRI systems. Because of large amount of image data generated by such modern medical scanners, there has been and remains a need for developing image processing techniques that can automate some or all of the processes to determine the presence of anatomical abnormalities in scanned medical images.

Digital medical images are constructed using raw image data obtained from a scanner, for example, a computerized axial tomography (CAT) scanner, magnetic resonance imaging (MRI), etc. Digital medical images are typically either a two-dimensional ("2D") image made of pixel elements, a three-dimensional ("3D") image made of volume elements ("voxels") or a four-dimensional ("4D") image made of dynamic elements ("doxels"). Such 2D, 3D or 4D images are processed using medical image recognition techniques to determine the presence of anatomical abnormalities or pathologies, such as cysts, tumors, polyps, etc. Given the amount of image data generated by any given image scan, it is preferable that an automatic technique should point out anatomical features in the selected regions of an image to a doctor for further diagnosis of any disease or condition.

Automatic image processing and recognition of structures within a medical image are generally referred to as Computer-Aided Detection (CAD). A CAD system can process medical images, localize and segment anatomical structures, including possible abnormalities (or candidates), for further review. Recognizing anatomical structures within digitized medical images presents multiple challenges. For example, a first concern relates to the accuracy of recognition of anatomical structures within an image. A second area of concern is the speed of recognition. Because medical images are an aid for a doctor to diagnose a disease or condition, the speed with which an image can be processed and structures within that image recognized can be of the utmost importance to the doctor in order to reach an early diagnosis.

Medical images play an important role in the correct diagnosis of diseases, such as Interstitial Lung Disease (ILD). ILD denotes a group of common lung diseases affecting the interstitium. ILD concerns alveolar epithelium, pulmonary capillary endothelium, basement membranes, perivascular and perilymphatic tissues. ILD causes gradual alteration of the lung tissues and leads to breathing dysfunction. It includes, but is not limited to, interstitial pneumonia, emphysema, sarcoidosis, and tuberculosis. FIGS. 1a-c show lung images with different types of ILD. More particularly, FIG. 1a shows an image 102 of a lung with emphysema; FIG. 1b shows an image 104 of a lung with usual interstitial pneumonia; and FIG. 1c shows an image 106 of a lung with sarcoidosis.

With image-based analysis, patients may not need to go through more invasive diagnostic methods such as surgical lung biopsy. One of the most commonly used imaging modalities for diagnosis of ILD is high-resolution computed tomography (HRCT). HRCT has the following advantages compared to other commonly used image modalities, such as X-ray and magnetic resonance imaging (MRI): first, three-dimensional HRCT data avoids superposition of organs and provides high in-plane resolution to facilitate recognition of patterns and distribution of lung tissues; and second, unlike MRI, which is only sensitive to inflammatory changes of pulmonary parenchyma, HRCT accurately depicts image appearance of different disease patterns, such as fibrosis and micro-nodule clusters.

Radiologists typically need to perform multiple screenings for ILD in their daily work. Because of the complex nature of ILD and anatomical variety of different patients, it is hard for radiologists to quickly and accurately make the diagnostic decision for ILD.

SUMMARY

Described herein is a framework for automatic retrieval of medical images. In accordance with one aspect, the framework detects patches in a query image volume that contain at least a portion of an anatomical region of interest by using a first trained classifier. The framework determines disease probabilities by applying a second trained classifier to the detected patches, and selects, from the patches, a sub-set of informative patches with disease probabilities above a predetermined threshold value. For a given patch from the sub-set of informative patches, the framework retrieves, from a database, patches that are most similar to the given image. Image volumes associated with the retrieved patches are then retrieved from the database. A report based on the retrieved image volumes may then be generated and presented.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

FIG. 4 shows an exemplary method of automatic medical image retrieval by a computer system;

DETAILED DESCRIPTION

Figure 1:
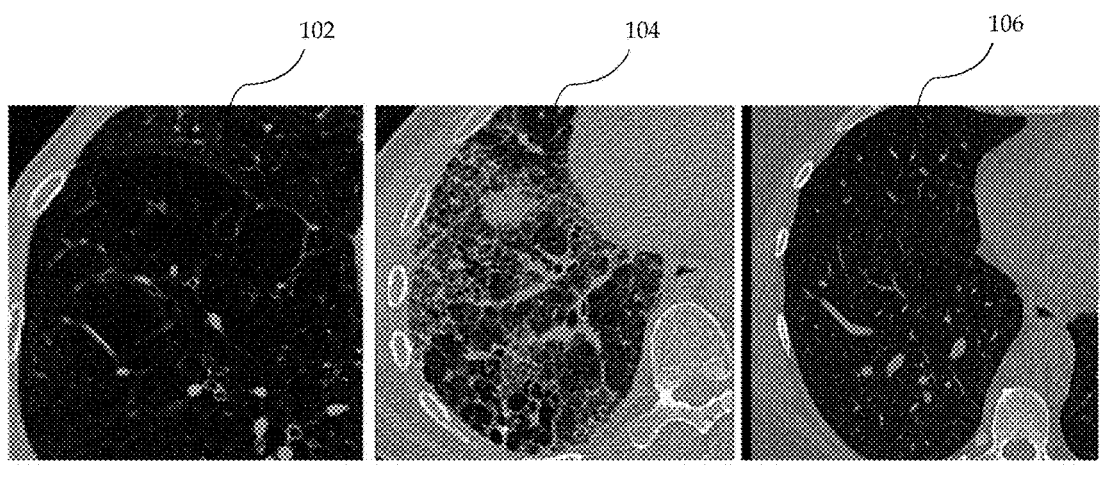
FIGS. 1a-c show lung images with different types of Interstitial Lung Disease (ILD)

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed; on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to high-resolution computed tomography (HRCT), x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, and "voxels" for volume image elements, often used with respect to 3D imaging, can be used interchangeably. It should be noted that the 3D volume image is itself synthesized from image data obtained as pixels on a 2D sensor array and displayed as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein.

Existing image collections with confirmed disease (e.g., ILD) diagnoses can help radiologists make appropriate diagnoses. Specifically, if images with disease patterns and anatomical structures similar to the query image can be fetched from large image collections in an efficient manner, they can provide valuable computer-aided diagnostic support to help radiologists make the diagnostic decision. The fetched images may also serve as evidence for reporting the diagnosis of the disease. Manual selection of similar images from the image collections is typically infeasible due to the huge size of such image collections. Current image retrieval methods in the computer vision domain mainly depend on ad-hoc hand-crafted features extracted from images. However, the appearances of diseases have very large variances in terms of scale, texture and spatial location, thereby making it unclear what features may be good for disease image retrieval.

A framework for automatic medical image retrieval is described herein. In accordance with one aspect, the framework trains classifiers to recognize anatomical sections and diseases based on the medical images. Using the trained classifiers, the framework fetches medical images from large image collections with disease patterns (e.g., emphysema, cystic fibrosis) and anatomical structures similar to the input query image to help radiologists make diagnostic decisions. For example, given a lung image volume, the framework retrieves a set of lung image volumes with similar disease patterns from the database.

The present framework solves a content-based medical image retrieval problem (i.e., finding images with a specific content in a larger set of images) by employing machine learning to automatically and efficiently recognize features, instead of using ad-hoc manually-designed features. The present framework improves the throughput of the disease diagnostic workflow by efficiently fetching similar images from large image collections. The reporting aspect is advantageously improved since the fetched images can be used to automatically populate and serve as evidence in case reports. These and other features and advantages will be described in more details herein.

Figure 2:
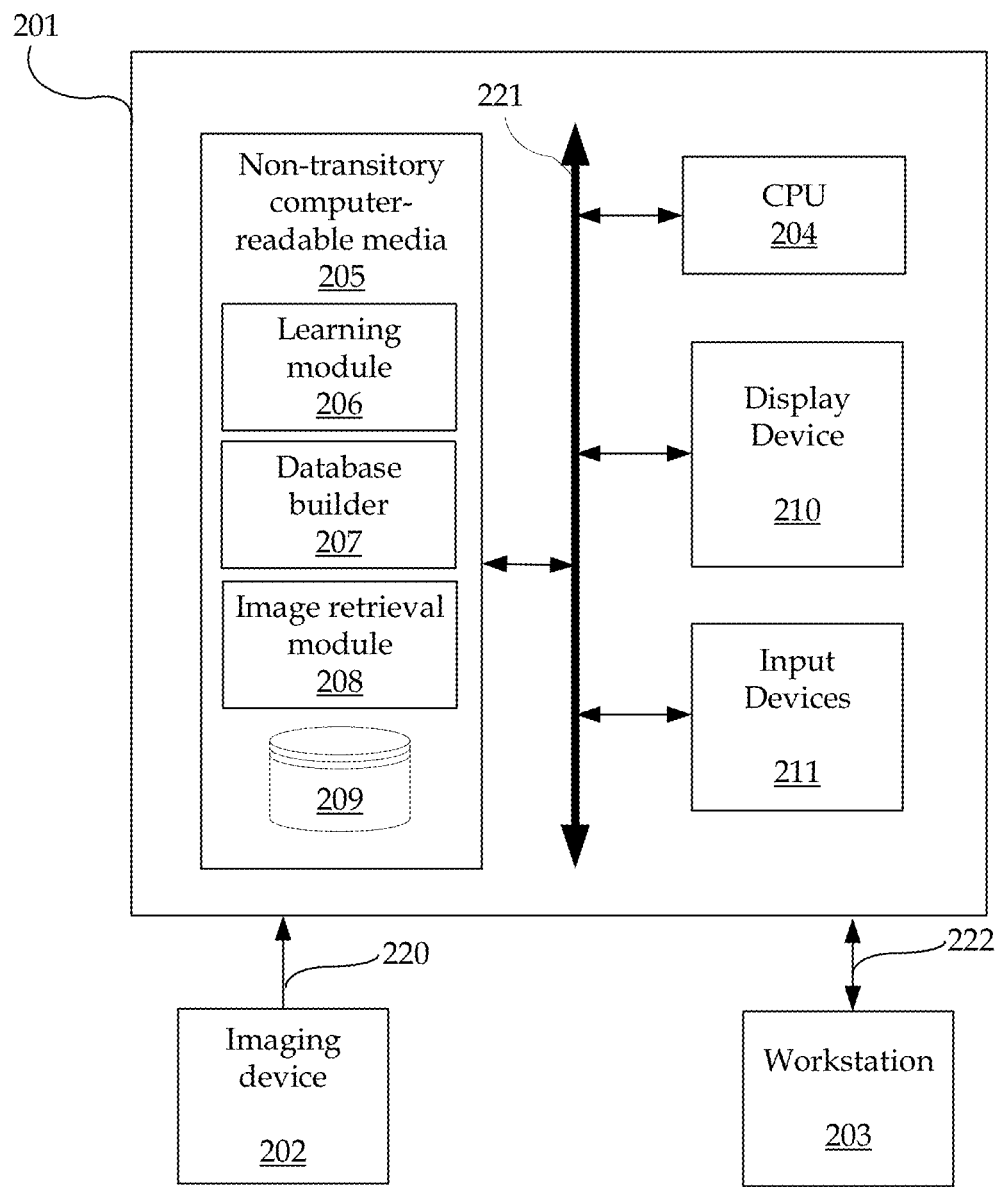
FIG. 2 is a block diagram illustrating an exemplary system.

FIG. 2 is a block diagram illustrating an exemplary system 200. The system 200 includes a computer system 201 for implementing the framework as described herein. In some implementations, computer system 201 operates as a standalone device. In other implementations, computer system 201 may be connected (e.g., using a network) to other machines, such as imaging device 202 and workstation 203. In a networked deployment, computer system 201 may operate in the capacity of a server (e.g., thin-client server), a cloud computing platform, a client user machine in server-client user network environment, or as a peer machine in a peer-to-peer (or distributed) network environment.

In some implementations, computer system 201 comprises a processor or central processing unit (CPU) 204 coupled to one or more non-transitory computer-readable media 205 (e.g., computer storage or memory), display device 210 (e.g., monitor) and various input devices 211 (e.g., mouse or keyboard) via an input-output interface 221. Computer system 201 may further include support circuits such as a cache, a power supply, clock circuits and a communications bus. Various other peripheral devices, such as additional data storage devices and printing devices, may also be connected to the computer system 201.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in non-transitory computer-readable media 205. In particular, the present techniques may be implemented by learning module 206, database builder 207, image retrieval module 208 and database 209.

Non-transitory computer-readable media 205 may include random access memory (RAM), read-only memory (ROM), magnetic floppy disk, flash memory, and other types of memories, or a combination thereof. The computer-readable program code is executed by CPU 204 to process medical data retrieved from, for example, database 209. As such, the computer system 201 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 205 may be used for storing a database (or dataset) 209. Such data may also be stored in external storage or other memories. The external storage may be implemented using a database management system (DBMS) managed by the CPU 204 and residing on a memory, such as a hard disk, RANI, or removable media. The external storage may be implemented on one or more additional computer systems. For example, the external storage may include a data warehouse system residing on a separate computer system, a cloud platform or system, a picture archiving and communication system (PACS), or any other hospital, medical institution, medical office, testing facility, pharmacy or other medical patient record storage system.

Imaging device 202 acquires medical images 220 associated with at least one patient. Such medical images 220 may be processed and stored in database 209. Imaging device 202 may be a radiology scanner (e.g., HRCT scanner) and/or appropriate peripherals (e.g., keyboard and display device) for acquiring, collecting and/or storing such medical images 220.

The workstation 203 may include a computer and appropriate peripherals, such as a keyboard and display device, and can be operated in conjunction with the entire system 200. For example, the workstation 203 may communicate directly or indirectly with the imaging device 202 so that the medical image data acquired by the imaging device 202 can be rendered at the workstation 203 and viewed on a display device. The workstation 203 may also provide other types of medical data 222 of a given patient. The workstation 203 may include a graphical user interface to receive user input via an input device (e.g., keyboard, mouse, touch screen voice or video recognition interface, etc.) to input medical data 222.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 3A:
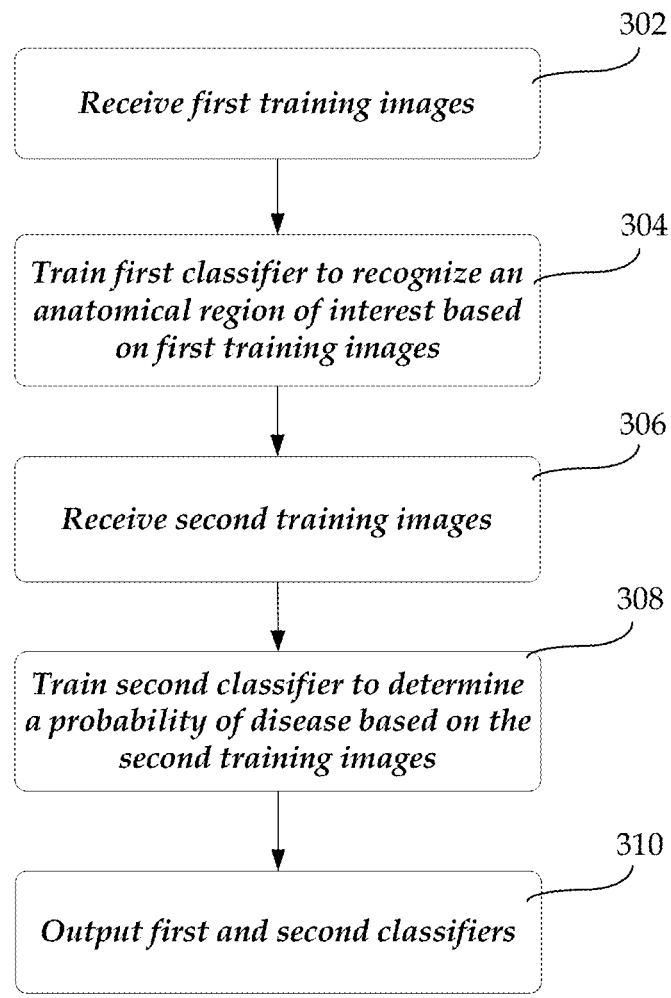
FIG. 3a shows an exemplary method of machine learning for image retrieval by a computer system.

FIG. 3a shows an exemplary method 300 of machine learning for image retrieval by a computer system. It should be understood that the steps of the method 300 may be performed in the order shown or a different order. Additional, different, or fewer steps may also be provided. Further, the method 300 may be implemented with the system 201 of FIG. 2, a different system, or a combination thereof.

At 302, learning module 206 receives first training images. The first training images may be acquired using techniques such as high-resolution computed tomography (HRCT), magnetic resonance (MR) imaging, computed tomography (CT), helical CT, X-ray, angiography, positron emission tomography (PET), fluoroscopy, ultrasound, single photon emission computed tomography (SPECT), or a combination thereof. The first training images may be retrieved from, for example, database 209. The first training images may include multiple sets of 2D patches corresponding to multiple image volumes. The 2D patches may be derived by continuously moving a sliding window within an image volume by a pre-determined distance (e.g., 3 voxels) in each direction (e.g., X, Y and/or Z) to generate non-overlapping patches. The size of the sliding window is the size of each patch, and may be, for example, 32 millimeters by 32 millimeters. Alternatively, the first training images may be a set of 3D images.

At 304, learning module 206 trains a first classifier to recognize the anatomical region of interest based on the first training images. The anatomical region of interest is a body portion that has been identified for investigation. The anatomical region of interest may be at least a section of a subject's lungs, brain, heart, spine, vertebra, blood vessel, aorta, and so forth. The first classifier is trained by using the first training images as input to a first learning architecture to identify input images that contain at least a portion of the particular anatomical region.

In some implementations, the first learning architecture is an unsupervised learning architecture that automatically discovers representations needed for feature detection instead of relying on labeled input. The first learning architecture may be a deep learning architecture that includes stacked layers of learning nodes. The first classifier may be represented by, for example, a convolutional neural network (CNN) classifier. CNN is a class of deep, feed-forward artificial neural network that uses a variation of multilayer perceptrons designed to require minimal preprocessing. The CNN architecture may include an input and an output layer, as well as multiple hidden layers. The hidden layers are either convolutional, pooling or fully connected. Convolutional layers apply a convolution operation to the input, passing the result to the next layer, thereby emulating the response of an individual neuron to visual stimuli. Pooling layers combine the outputs of neuron clusters at one layer into a single neuron in the next layer, while fully connected layers connect every neuron in one layer to every neuron in another layer. Other types of classifiers, such as random forests, may also be used.

At 306, learning module 206 receives second training images of the particular anatomical region of interest. The second training images may be retrieved from, for example, database 209. The second training images may include multiple sets of 2D patches corresponding to multiple image volumes of a particular anatomical region of interest (e.g., lung). The 2D patches may be derived by continuously moving a sliding window within an image volume by a pre-determined distance (e.g., 3 voxels) in each direction (e.g., X, Y and/or Z) to generate non-overlapping patches that include at least a portion of the anatomical region of interest. The size of the sliding window is the size of each patch, and may be, for example, 32 millimeters by 32 millimeters. Alternatively, the second training images may be a set of 3D images.

At 308, learning module 206 trains a second classifier to determine a probability of disease based on the second training images. The second classifier is trained by using the second training images as input to a second learning architecture to identify probabilities of disease in the anatomical region of interest. In some implementations, the second classifier outputs a vector indicating the probability of disease in the anatomical region of interest in an input image. Each probability of disease may range from, for example, 0 to 100%. The disease may be, for example, emphysema, cystic fibrosis or other types of lung disease.

The second learning architecture may be an unsupervised learning architecture automatically discovers representations needed for feature detection instead of relying on labeled input. The second learning architecture may be a deep learning architecture that includes stacked layers of learning nodes. The second classifier may be represented by, for example, a convolutional neural network (CNN) architecture. Other types of classifiers, such as random forests, may also be used.

At 310, learning module 206 outputs the first and second classifiers to database builder 207 and image retrieval module 208. The database builder 207 may use the first and second classifiers to construct a database 209 of images for reference. The image retrieval module 208 may use the first and second classifiers to retrieve images from database 209 that are most similar to a query image.

Figure 3B:
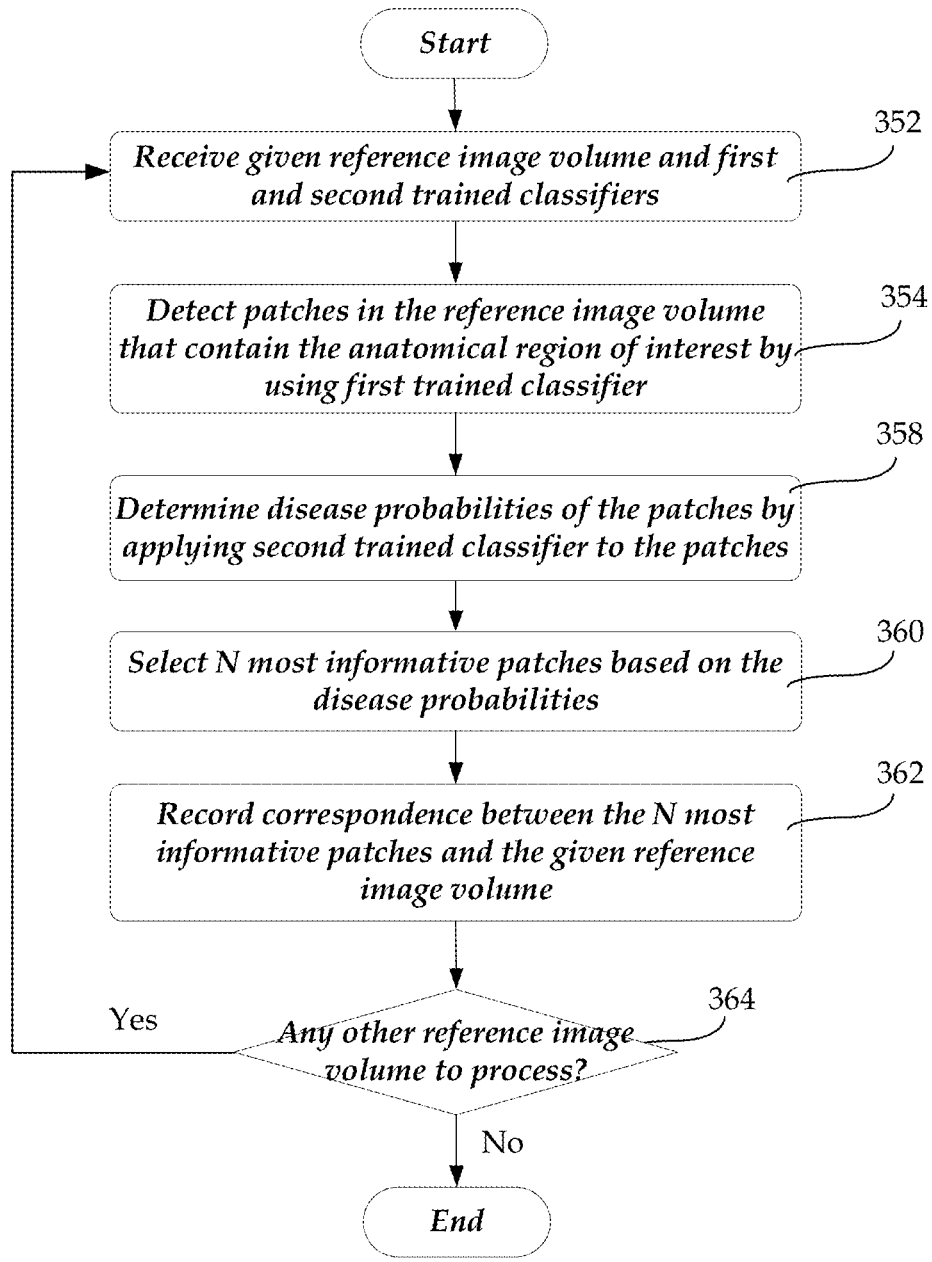
FIG. 3b shows an exemplary method of constructing a database by a computer system.

FIG. 3b shows an exemplary method 350 of constructing a database by a computer system. It should be understood that the steps of the method 350 may be performed in the order shown or a different order. Additional, different, or fewer steps may also be provided. Further, the method 350 may be implemented with the system 201 of FIG. 2, a different system, or a combination thereof.

At 352, database builder 207 receives a given reference image volume and first and second trained classifiers. The reference image volume may be retrieved from a large collection of K reference image volumes with confirmed disease diagnoses. K is a positive integer that is much larger than N, where N represents the number of most informative patches to be selected from each reference image volume. The reference image volume is acquired by the same modality used to acquire the training images for training the first and second trained classifiers (e.g., HRCT, X-ray, etc.). In some implementations, the reference image volume contains 2D patches. Other types of reference image volume are also useful. The first and second trained classifiers may be trained by learning module 206 as previously described with reference to FIG. 3a. The first and second trained classifiers may be, for example, convolutional neural network (CNN) classifiers.

At 354, database builder 207 detects reference patches that contain at least a portion of the anatomical region of interest by applying the first trained classifier to the reference image volume. In some implementations, the reference patches are detected by moving a sliding window in the reference image volume by a predetermined distance (e.g., 3 voxels) in at least one direction (e.g., X, Y and/or Z), and applying the first trained classifier to the image data within the window to detect patches that contain at least a portion of the anatomical region of interest (e.g., lung tissue). The size of the window is the size of each patch and may be, for example, 32 millimeters by 32 millimeters.

At 358, database builder 207 determines disease probabilities of the patches that contain the anatomical region of interest by applying the second trained classifier to the set of reference patches. In some implementations, for each patch, the second classifier outputs a vector indicating the probability of lung disease (e.g., interstital lung disease). Other types of disease probabilities may also be determined.

At 360, database builder 207 selects N most informative patches based on the disease probabilities. The N most informative patches are those with disease probabilities above a pre-determined threshold. N is a positive integer that is less than the total number of patches in the set of patches.

At 362, database builder 207 records the correspondence (or association) between the N most informative patches and the given reference image volume. The correspondence may be recorded in, for example, a mapping table in database 209.

At 364, database builder 207 determines if there is any other reference image volume to be processed. If yes, steps 352 through 362 are repeated to process the next reference image volume. If no, the method 350 ends.

FIG. 4 shows an exemplary method 400 of automatic medical image retrieval by a computer system. It should be understood that the steps of the method 400 may be performed in the order shown or a different order. Additional, different, or fewer steps may also be provided. Further, the method 400 may be implemented with the system 201 of FIG. 2, a different system, or a combination thereof.

At 402, image retrieval module 208 receives a query image volume and first and second trained classifiers. The query image volume may be provided by the user via, for example, a user interface implemented at workstation 203. The user may desire to retrieve, from database 209, reference image volume that is most similar to the query image volume. The query image volume is acquired by the same modality used to acquire the training images for training the first and second trained classifiers (e.g., HRCT, X-ray, etc.). In some implementations, the query image volume contains 2D patches. Other types of query image volumes are also useful. The first and second trained classifiers may be trained by learning module 206 as previously described with reference to FIG. 3*a*. The first and second trained classifiers may be, for example, convolutional neural network (CNN) classifiers.

At 404, image retrieval module 208 detects patches in the query image volume that contain the anatomical region of interest by applying the first trained classifier to the query image volume. In some implementations, the patches are detected by sliding a window in the query image volume by a predetermined distance (e.g., 3 voxels) in at least one direction (e.g., X, Y and/or Z) and applying the first trained classifier to the query image portion within the window to detect patches that contain at least a portion of the anatomical region of interest (e.g., lung tissue). The size of the window is the size of each patch, and may be, for example, 32 millimeters by 32 millimeters.

At 408, image retrieval module 208 determines disease probabilities of the patches by applying the second trained classifier to the set of patches. In some implementations, for each patch, the second classifier outputs a vector indicating the probability of lung disease (e.g., interstital lung disease, emphysema).

At 410, image retrieval module 208 selects N most informative patches based on the disease probabilities. The N most informative patches are those with disease probabilities above a pre-determined threshold. N is a positive integer that is less than the total number of patches in the set of patches.

At 412, for each given informative patch, image retrieval module 208 retrieves, from the database 209, M patches that are most similar to the given informative patch. M is a positive integer that is less than the total number of patches corresponding to a given image volume. A total of N*M local patches may be retrieved from the database 209. The database 209 may be created by the database builder 207 as previously described with reference to FIG. 3*b*.

At 414, image retrieval module 208 retrieves, from the database 209, one or more most similar image volumes that are associated with (or correspond to) the retrieved patches. The image volumes may be identified by, for example, looking up a mapping table that maps each patch to a particular image volume.

At 416, image retrieval module 208 generates a report based on the retrieved most similar image volumes. The report may be presented at, for example, workstation 203. The report may be presented in a series of interactive user interface screens to enable efficient user review of the anomalous anatomical region with potential indications of associated conditions or disease from the retrieved images. The report may relate the query image volume to the retrieved image volumes as evidence for supporting diagnostic decision, therapy and/or patient management. The user may also access medical records (e.g., patient history, diagnoses, treatments) associated with the retrieved image volumes to support diagnostic decisions. In some implementations, image retrieval module 208 generates a visualization of anatomical similarity in the report by highlighting similar disease patterns and/or image appearances within the local anatomical region of interest in both the retrieved image volumes and the query image volume.

Image retrieval module 208 may further identify a suitable therapy for the patient associated with the query image volume based on medical records (e.g., patient histories, prior treatments) associated with the most similar image volumes and/or using relevant information from collections of published peer reviewed journals and clinical data. A recommendation of the identified treatment may then be presented in the report.

Figure 5:
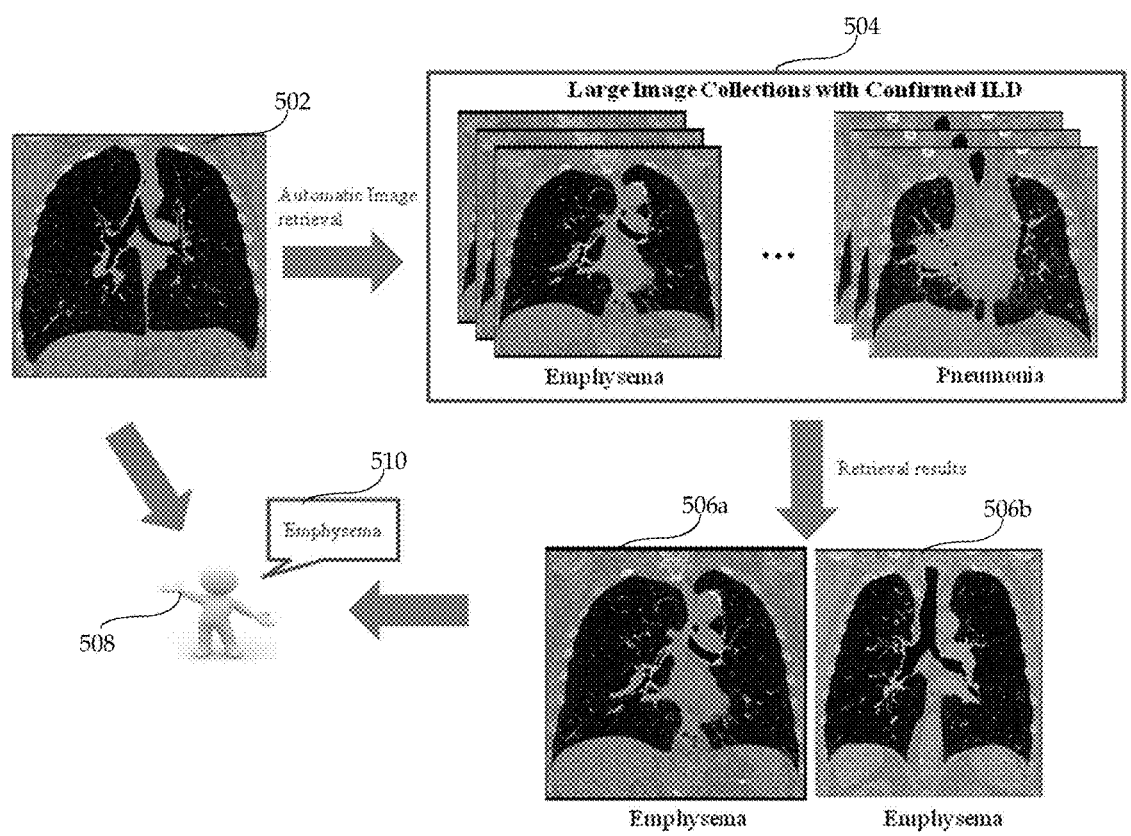
FIG. 5 shows an exemplary workflow that one implementation of the present framework facilitates.

FIG. 5 shows an exemplary workflow that one implementation of the present framework facilitates. The query image volume 502 is provided to the image retrieval module 208. The image retrieval module 208 then retrieves images 506*a-b* from a large image collection 504 of images with confirmed ILD. The retrieved images 506*a-b* are then presented to the user (e.g., radiologist) 508 in an evidence-based report. The user 508 then provides the final diagnostic decision 510 based on the query image volume 502, retrieval results 506*a-b* and other information (e.g., patient history).

Figure 6:
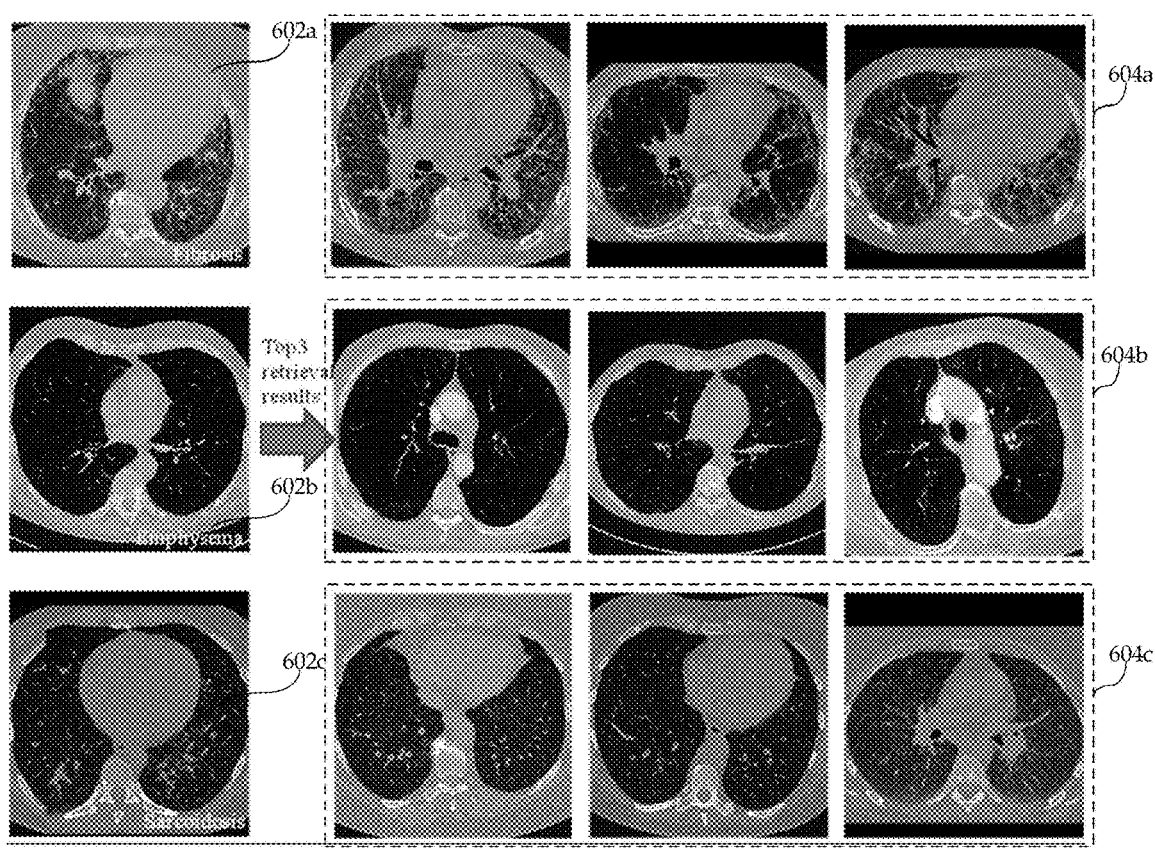
FIG. 6 shows exemplary results generated by the present framework.

Additional examples, illustrated in FIG. 6, show query images with corresponding top three retrieval images. Image volumes 602*a-c* are provided to the image retrieval module 208. More particularly, image volume 602*a* represents lung tissue with fibrosis, image volume 602*b* represents lung tissue with emphysema, and image volume 602*c* represents lung tissue with sarcoidosis. Based on these image volumes 602*a-c*, image retrieval module 208 then retrieves from database 209 the top 3 most similar image volumes 604*a-c* for each image volume 602*a-c*.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A system for image retrieval, comprising:
 a non-transitory memory device for storing computer readable program code; and
 a processor device in communication with the memory device, the processor being operative with the computer readable program code to perform steps including
 constructing a database by using first and second trained classifiers,
 receiving a query image volume,
 detecting patches that contain at least a portion of a lung by applying the first trained classifier to the query image volume,
 determining lung disease probabilities by applying the second trained classifier to the detected patches,
 selecting, from the patches, a sub-set of informative patches with the lung disease probabilities above a pre-determined threshold value,
 for a given patch from the sub-set of informative patches, retrieving, from the database, one or more patches that are most similar to the given patch,
 retrieving, from the database, image volumes associated with the retrieved patches, and
 generating and presenting a report based on the retrieved image volumes.

2. The system of claim 1 wherein the processor is operative with the computer readable program code to construct the database by detecting reference patches that contain at least a portion of the lung by applying the first trained classifier to a given reference image volume, determining lung disease probabilities by applying the second trained classifier to the detected reference patches, selecting, from the detected reference patches, a sub-set of informative patches with the disease probabilities above a pre-determined threshold value, and recording a correspondence between the sub-set of informative patches and the given reference image volume.

3. The system of claim 1 wherein the processor is operative with the computer readable program code to train the first and second classifiers using convolutional neural networks.

4. The system of claim 1 wherein the processor is operative with the computer readable program code to detect the patches that contain at least a portion of the anatomical region of interest by sliding a window in the query image volume by a predetermined distance in at least one direction and applying the first trained classifier to a portion of the query image volume within the window.

5. A method of image retrieval, comprising:
receiving a query image volume and first and second trained classifiers;
detecting patches that contain at least a portion of an anatomical region of interest by applying the first trained classifier to the query image volume;
determining disease probabilities by applying the second trained classifier to the detected patches;
selecting, from the patches, a sub-set of informative patches with the disease probabilities above a pre-determined threshold value;
for a given patch from the sub-set of informative patches, retrieving, from a database, one or more patches that are most similar to the given patch;
retrieving, from the database, one or more image volumes associated with the retrieved patches; and
generating and presenting a report based on the one or more retrieved image volumes.

6. The method of claim 5 further comprises training the first classifier based on first training patches to recognize the anatomical region of interest, wherein the first training patches are extracted by moving a sliding window within an image volume.

7. The method of claim 6 wherein training the first classifier comprises applying the first training patches as input to an unsupervised learning architecture.

8. The method of claim 7 wherein the unsupervised learning architecture comprises a convolutional neural network classifier.

9. The method of claim 5 further comprises training the second classifier based on second training patches to determine a probability of disease in the anatomical region of interest, wherein the second training patches are extracted by moving a sliding window within an image volume.

10. The method of claim 9 wherein training the second classifier comprises applying the second training patches as input to an unsupervised learning architecture.

11. The method of claim 10 wherein the unsupervised learning architecture comprises a convolutional neural network classifier.

12. The method of claim 5 further comprises constructing the database by using the first and second trained classifiers.

13. The method of claim 12 wherein constructing the database comprises:

(i) detecting reference patches that contain at least a portion of the anatomical region of interest by applying the first trained classifier to a given reference image volume;

(ii) determining disease probabilities by applying the second trained classifier to the detected reference patches;

(iii) selecting, from the detected reference patches, a sub-set of informative patches with the disease probabilities above a pre-determined threshold value; and (iv) recording a correspondence between the sub-set of informative patches and the given reference image volume.

14. The method of claim 13 wherein detecting the reference patches that contain at least a portion of the anatomical region of interest comprises moving a sliding window in the reference image volume and applying the first trained classifier to the image volume within the window to detect patches that contain the at least a portion of the anatomical region of interest.

15. The method of claim 13 further comprises repeating operations (i), (ii), (iii) and (iv) to process other reference image volumes in the database.

16. The method of claim 5 wherein detecting the patches that contain at least a portion of the anatomical region of interest comprises sliding a window in the query image volume by a predetermined distance in at least one direction and applying the first trained classifier to a portion of the query image volume within the window.

17. The method of claim 5 wherein retrieving the one or more image volumes associated with the retrieved patches comprises looking up a mapping table that maps the retrieved patches to one or more image volumes.

18. The method of claim 5 wherein generating and presenting the report based on the one or more retrieved image volumes comprises generating a series of interactive user interface screens to enable efficient user review of the anatomical region of interest.

19. The method of claim 5 wherein generating and presenting the report based on the one or more retrieved image volumes comprises generating a visualization that highlights similar disease patterns or image appearances within the anatomical region of interest in the query image volume and the one or more retrieved image volumes.

20. One or more non-transitory computer readable media embodying a program of instructions executable by a machine to perform operations for processing medical image data, the operations comprising:
receiving a query image volume and first and second trained classifiers;
detecting patches that contain at least a portion of an anatomical region of interest by applying the first trained classifier to the query image volume;
determining disease probabilities by applying the second trained classifier to the detected patches;
selecting, from the patches, a sub-set of informative patches with the disease probabilities above a pre-determined threshold value;
for a given patch from the sub-set of informative patches, retrieving, from a database, one or more patches that are most similar to the given patch;
retrieving, from the database, image volumes associated with the retrieved patches; and
generating and presenting a report based on the retrieved image volumes.

* * * * *